(12) United States Patent
Gao et al.

(10) Patent No.: US 11,337,447 B2
(45) Date of Patent: May 24, 2022

(54) PLANOCOCCUS AND METHOD FOR IMPROVING FERMENTATION QUALITY OF LOW-SALT FISH SAUCE BY PLANOCOCCUS

(71) Applicant: Jiangsu University, Jiangsu (CN)

(72) Inventors: Ruichang Gao, Jiangsu (CN); Jing Zhou, Jiangsu (CN); Li Yuan, Jiangsu (CN); Yue Zhou, Jiangsu (CN)

(73) Assignee: Jiangsu University, Jiangsu (CN)

( * ) Notice: Subject to any disclaimer, the term of this patent is extended or adjusted under 35 U.S.C. 154(b) by 0 days.

(21) Appl. No.: 17/256,008

(22) PCT Filed: May 27, 2020

(86) PCT No.: PCT/CN2020/092490
§ 371 (c)(1),
(2) Date: Dec. 24, 2020

(87) PCT Pub. No.: WO2021/143006
PCT Pub. Date: Jul. 22, 2021

(65) Prior Publication Data
US 2021/0401009 A1    Dec. 30, 2021

(30) Foreign Application Priority Data

Jan. 13, 2020  (CN) .......................... 202010025134.4
Jan. 13, 2020  (CN) .......................... 202010076088.0

(51) Int. Cl.
*A23L 17/00* (2016.01)
*A23L 17/20* (2016.01)
(Continued)

(52) U.S. Cl.
CPC .............. *A23L 17/65* (2016.08); *A23L 17/20* (2016.08); *A23L 27/24* (2016.08); *C12N 1/20* (2013.01); *C12R 2001/07* (2021.05)

(58) Field of Classification Search
CPC .......... A23L 17/20; A23L 27/24; C12N 1/20; C12N 1/22; C12R 2001/07
(Continued)

(56) References Cited

FOREIGN PATENT DOCUMENTS

| CN | 104642998 | 5/2015 |
|----|-----------|--------|
| CN | 105901651 | 8/2016 |

(Continued)

OTHER PUBLICATIONS

CN-105901651—English Abstract (Year: 2016).*

(Continued)

*Primary Examiner* — Hamid R Badr
(74) *Attorney, Agent, or Firm* — JCIP Global Inc.

(57) ABSTRACT

The present invention discloses *Planococcus* and a method for improving fermentation quality of a low-salt fish sauce by *Planococcus*, and relates to the application field of food microbiology technology. The *Planococcus* strains have been deposited in China General Microbiological Culture Collection Center (CGMCC) under CGMCC NO. 17057, CGMCC NO. 17058, CGMCC NO. 17059, and CGMCC NO. 17060. The production cycle of fermented fish sauce using the *Planococcus* strains is greatly shortened, and the fermentation temperature is reduced. The fish sauce obtained by this method is transparent brown red, and has the unique aroma of aquatic products without impurities such as suspension or flocculent. The finished fish sauce has low salt content and high amino acid nitrogen content (according to the Chinese fish sauce industry standard, the fish sauce is classified as first-grade fish sauce). The contents of total volatile basic nitrogen and histamine are lower than the national standard.

5 Claims, 8 Drawing Sheets

(51) Int. Cl.
*A23L 27/24* (2016.01)
*C12N 1/20* (2006.01)
*C12R 1/07* (2006.01)

(58) Field of Classification Search
USPC .............................................. 426/7
See application file for complete search history.

(56) References Cited

FOREIGN PATENT DOCUMENTS

| | | |
|---|---|---|
| CN | 106191139 | 12/2016 |
| CN | 108611291 | 10/2018 |

OTHER PUBLICATIONS

Yoon, J-H. et al. Int. J. system. & evolutionary Microbiol. 53: 2013-2017 (Year: 2003).*
"International Search Report (Form PCT/ISA/210)" of PCT/CN2020/092490, dated Oct. 14, 2020, pp. 1-5.
"Written Opinion of the International Searching Authority (Form PCT/ISA/237)" of PCT/CN2020/092490, dated Oct. 14, 2020, pp. 1-4.

* cited by examiner

PLANOCOCCUS AND METHOD FOR IMPROVING FERMENTATION QUALITY OF LOW-SALT FISH SAUCE BY PLANOCOCCUS

CROSS-REFERENCE TO RELATED APPLICATION

This application is a 371 of international application of PCT application serial no. PCT/CN2020/092490, filed on May 27, 2020, which claims the priority benefit of China application no. 202010076088.0, filed on Jan. 13, 2020 and China application no. 202010025134.4, filed on Jan. 13, 2020. The entirety of each of the above mentioned patent applications is hereby incorporated by reference herein and made a part of this specification.

BACKGROUND

Technical Field

The present invention relates to the field of food microbial technology applications, and in particular to *Planococcus* and a method for improving fermentation quality of low-salt fish sauce by *Planococcus*.

Description of Related Art

China is a major fishery country, and freshwater aquaculture has become an important pillar of China's fishery industry. In 2017, China's total output of freshwater aquaculture was about 29.05 million tons, but the processing utilization rate was less than 15%, which caused waste of resources and environmental pollution. How to solve the problem of comprehensive utilization of freshwater fish is a major challenge facing China's aquatic product processing industry. Fish sauce is a traditional aquatic fermented condiment, which is one of the most popular condiments in Southeast Asia. First, the color is clear brownish red, with unique flavor and aroma, and has become part of people's daily diet. Traditional fish sauce production usually uses low-value fish and shrimp or aquatic processing waste (fish heads, offal, etc.) as raw materials and it is fermented by its own microorganisms. Fish sauce is rich in nutrients, contains a variety of essential amino acids, and mineral elements such as calcium, magnesium, zinc, and iron that are beneficial to the human body. It is a low-fat high-protein fermentation condiment. Fish sauce is also a value-added product of low-value fish, which has important practical significance for promoting the development of the freshwater fish industry. In the process of fish sauce fermentation, protease is mainly used to catalyze protein hydrolysis. According to the influence of temperature on the activity and stability of proteases, it can be divided into low-temperature protease, medium-temperature protease and high-temperature protease. Low-temperature protease is a type of cold-adapted protease produced by low-temperature bacteria under low-temperature conditions. Low-temperature protease has high catalytic efficiency at low temperature, and generally the most suitable reaction temperature is 20-40° C. Low-temperature protease can react at low temperature or room temperature without heating and cooling, which can reduce costs. Therefore, it has the superiority that medium temperature protease cannot replace in industrial production. It has broad application prospects in the fields of washing industry, food processing, biopharmaceuticals, environmental bioremediation, etc. *Planococcus* have been identified as cold-tolerant bacteria that produce low-temperature proteases, and have high safety. The present invention will utilize *Planococcus* strains to produce fish sauce under the condition of low temperature and low salt to obtain fish sauce products with short fermentation period, low salinity and high flavor and nutritional value, which provides the theoretical basis and method for the application of *Planococcus* in food fermentation.

SUMMARY

The invention obtains the *Planococcus* that can improve the fermentation quality of low-salt fish sauce from the traditional shrimp paste, and combines the growth characteristics and enzymatic characteristics of the *Planococcus* to produce the fish sauce. This method can effectively shorten the fermentation cycle and reduce the salt content and improve the flavor and nutritional value of fish sauce, so it can provide a more stable, safer and more suitable starter cultures for the fermentation of fish sauce.

The present invention provides the use of the strain of *Planococcus* for improving the flavor and quality of fish sauce fermentation.

A method for fermenting a fish sauce by using *Planococcus*, including the following steps:

(1) treatment of raw materials: mincing fish trimmings (wastes from fish flesh processing) with a mincer, and adding 5 to 15% (w/w) of a pickling sea salt thereto, followed by mixing well for future use;

(2) preparation of starter cultures: activating and culturing any one of *Planococcus maritimus* XJ2, *Planococcus plakortidis* XJ10, *Planococcus dechangensis* XJ11 and *Planococcus rifietoensis* XJ12 three times to obtain an activated bacterial suspension; centrifuging the activated bacterial suspension at 4° C. and 10000 r/min for 10 min to obtain cell pellets, and then washing the cell pellets twice with sterile physiological saline, then resuspending the cell pellets in a small amount of the sterile physiological saline to obtain a bacterial suspension, and finally adjusting a concentration of the bacterial suspension to $10^5$-$10^7$ CFU/mL for future use;

(3) addition of the starter cultures: according to a final addition amount ($10^5$-$10^9$ CFU/g), mixing the strain into the pretreated raw minced fish flesh, so that the final bacterial count meets addition requirements, thereby obtaining a mixture;

(4) fermentation of fish sauce: incubating and fermenting the mixture obtained in step (3) at a temperature of 15-30° C. for 5-30 days;

(5) filtration of the fish sauce: sterilizing the fish sauce sample obtained in step (4) at 120° C. for 10 to 30 mins, cooling the sterilized fish sauce sample to room temperature and then centrifuging it at 10000 r/min for 20 mins to obtain a supernatant, and then filtering the supernatant with multiple layers of gauze to remove solids and impurities;

(6) sterilization of the fish sauce: performing secondary sterilization on the fish sauce obtained in step (5) at 100° C. for 15 to 30 mins, followed by filling and sealing it under aseptic conditions to obtain a finished fish sauce; and (7) Evaluation of product physical and chemical indicators: amino acid nitrogen content evaluation, method refers to GB5009.235-2016 colorimetry; volatile base nitrogen content evaluation, method refers to GB5009.228-2016 micro-diffusion method; determination of histamine content, the method refers to GB5009.208-2016 spectrophotometry.

The *Planococcus* is *Planococcus maritimus* XJ2 or *Planococcus plakortidis* XJ10 or *Planococcus dechangensis* XJ11 or *Planococcus rifietoensis* XJ12.

A method for improving fermentation quality of a low-salt fish sauce by using mixed *Planococcus* strains, including the following steps:

(1) treatment of raw materials: mincing fish trimmings (wastes from fish flesh processing) with a mincer, and adding 5 to 15% (w/w) of a pickling sea salt thereto, followed by mixing well for future use;

(2) Preparation of mixed starter: activating and culturing each of *Planococcus maritimus* XJ2, *Planococcus plakortidis* XJ10, *Planococcus dechangensis* XJ11 and *Planococcus rifietoensis* XJ12 three times to obtain an activated bacterial suspension; centrifuging the activated bacterial suspension at 4° C. and 10000 r/min for 10 min to obtain cell pellets, and then washing the cell pellets twice with sterile physiological saline, then resuspending the cell pellets in a small amount of the sterile physiological saline to obtain a bacterial suspension, and finally adjusting a concentration of the bacterial suspension to $10^5$-$10^7$ CFU/mL for future use;

(3) addition of the mixed starter: mixing *Planococcus maritimus* XJ2, *Planococcus plakortidis* XJ10, *Planococcus dechangensis* XJ11 and *Planococcus rifietoensis* XJ12 according to a bacteria count ratio of (1-3): (1-3): (1-3): (1-3) to prepare the mixed starter, and according to a final addition amount ($10^5$-$10^9$ CFU/g), mixing the mixed starter into the pretreated raw minced fish flesh, so that the final bacterial count meets addition requirements, thereby obtaining a mixture;

(4) fermentation of fish sauce: incubating and fermenting the mixture obtained in step (3) at a temperature of 15-30° C. for 5-30 days;

(5) filtration of the fish sauce: sterilizing the fish sauce sample obtained in step (4) at 120° C. for 10 to 30 mins, cooling the sterilized fish sauce sample to room temperature and then centrifuging it at 10000 r/min for 20 mins to obtain a supernatant, and then filtering the supernatant with multiple layers of gauze to remove solids and impurities;

(6) sterilization of the fish sauce: performing secondary sterilization on the fish sauce obtained in step (5) at 100° C. for 15 to 30 mins, followed by filling and sealing it under aseptic conditions to obtain a finished fish sauce; and (7) Evaluation of product physical and chemical indicators: amino acid nitrogen content evaluation, method refers to GB5009.235-2016 colorimetry method; volatile base nitrogen content evaluation, method refers to GB5009.228-2016 micro-diffusion method; determination of histamine content, the method refers to GB5009.208-2016 spectrophotometry.

*Planococcus maritimus* XJ2, this strain has been deposited on Jan. 2, 2019 in the China General Microbiological Culture Collection Center (CGMCC), numbered CGMCC NO. 17057, suggested classification name: *Planococcus maritimus*.

*Planococcus plakortidis* XJ10, this strain has been deposited on Jan. 2, 2019 in the China General Microbiological Culture Collection Center (CGMCC), numbered CGMCC NO. 17058, suggested classification name: *Planococcus plakortidis*.

*Planococcus dechangensis* XJ11, this strain has been deposited on Jan. 2, 2019 in the Chinese General Microbiological Culture Collection Center (CGMCC), numbered CGMCC NO. 17059, suggested classification name: *Planococcus dechangensis*.

*Planococcus rifietoensis* XJ12, which has been deposited on Jan. 2, 2019 in the Chinese General Microbiological Culture Collection Center (CGMCC), numbered CGMCC NO. 17060, suggested classification name: *Planococcus rifietoensis*.

The beneficial effects of the present invention:

The fermentation cycle of fermented fish sauce using the above strains of *Planococcus* is greatly shortened, and the fermentation temperature is reduced. The fish sauce obtained by this method is transparent brown-red, with a unique aroma of aquatic products, and no impurities such as suspension or flocculent. Low salt content, high amino acid nitrogen content (the fish sauce is classified as first-class fish sauce according to the Chinese fish sauce industry standard), the content of volatile base nitrogen is low, and the content of histamine is lower than the national standard. The fish sauce is delicious and rich in nutrients, so the starter cultures can be used to produce green and safe fermented fish sauce products.

In summary, the present invention has possessed the uniqueness of the invention patent, achieved outstanding substantive features, and remarkable progress in innovation and practicality, which has produced beneficial effects.

DESCRIPTION OF THE EMBODIMENTS

Figure 1:
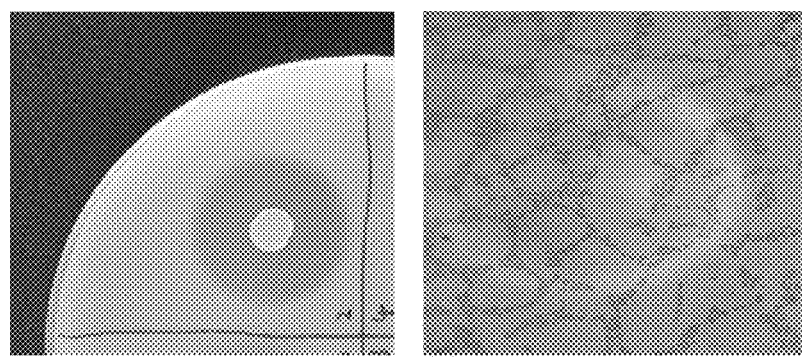
FIG. 1 shows the colony morphology and bacterial morphology of a *Planococcus* strain *Planococcus maritimus* XJ2.
Figure 2:
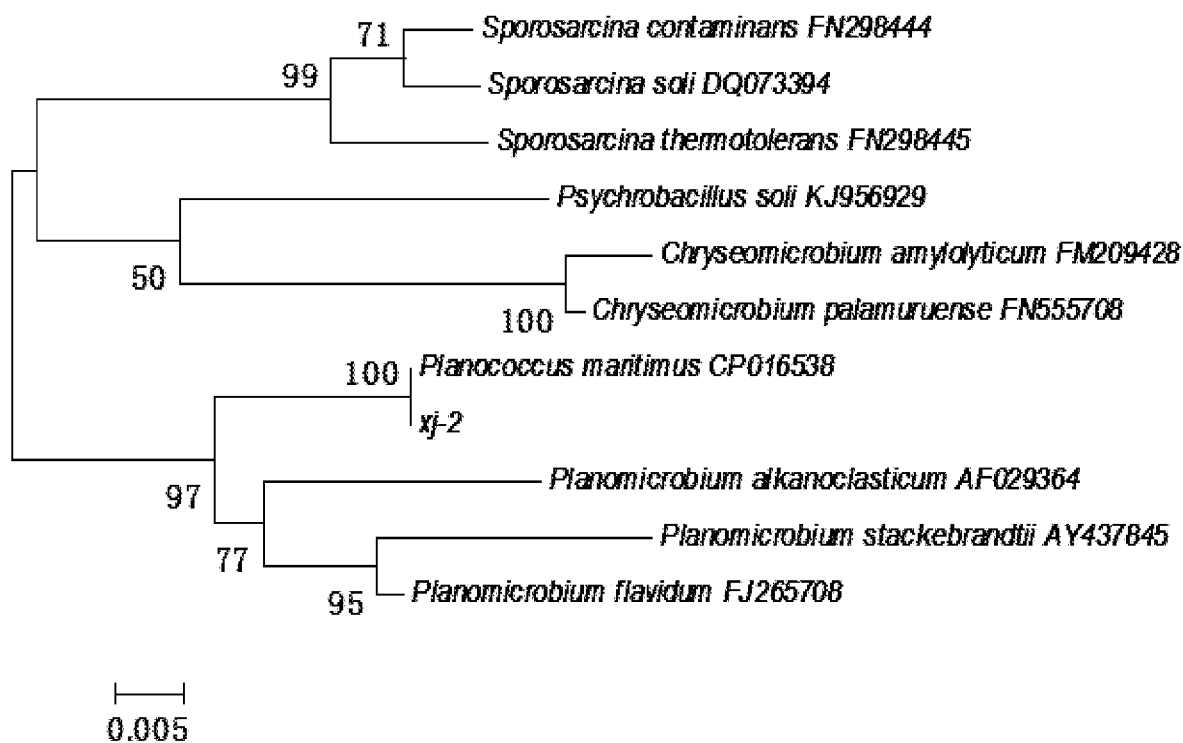
FIG. 2 shows the phylogenetic tree constructed by 16S rRNA sequence of the *Planococcus* strain *Planococcus maritimus* XJ2.
Figure 3:
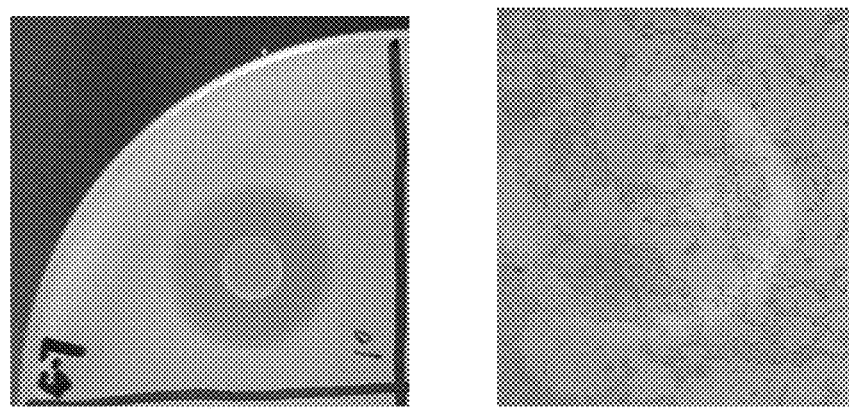
FIG. 3 shows the colony morphology and bacterial morphology of a *Planococcus* strain *Planococcus* plakortidis XJ10.
Figure 4:
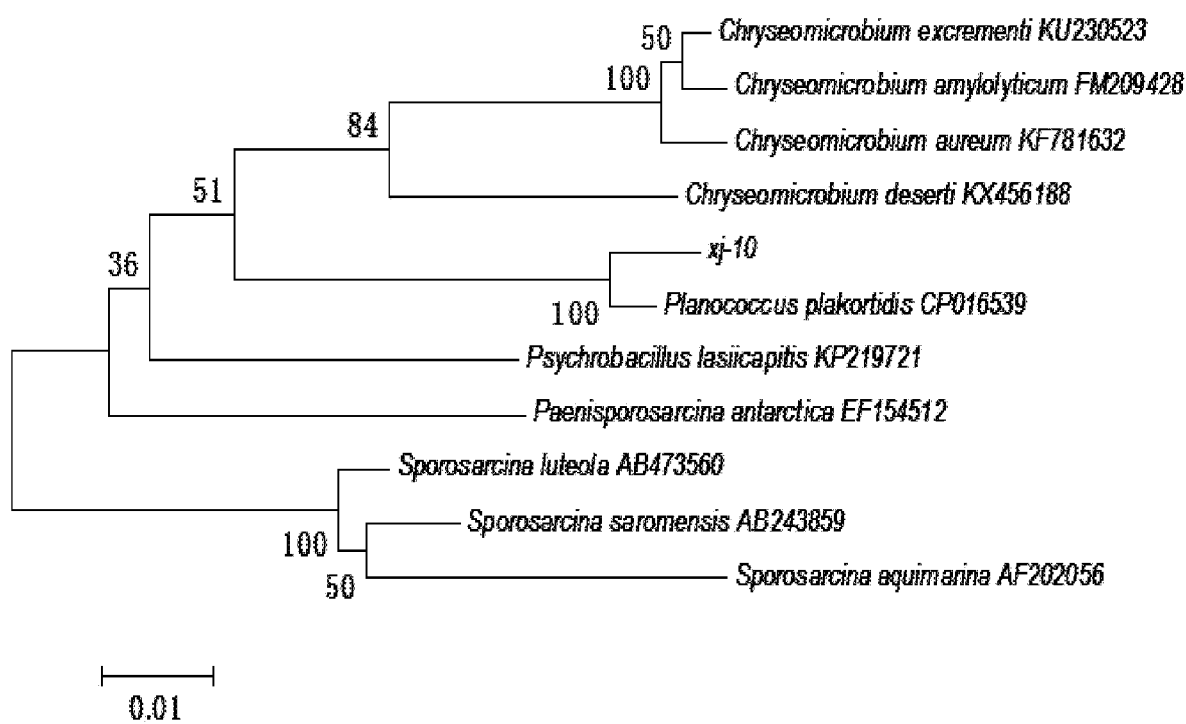
FIG. 4 shows the phylogenetic tree constructed by 16S rRNA sequence of the *Planococcus* strain *Planococcus* plakortidis XJ10.
Figure 5:
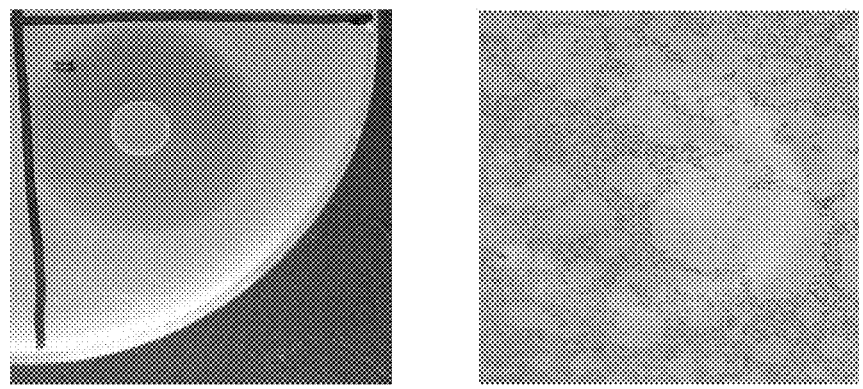
FIG. 5 shows the colony morphology and bacterial morphology of a *Planococcus* strain *Planococcus* dechangensis XJ11.
Figure 6:
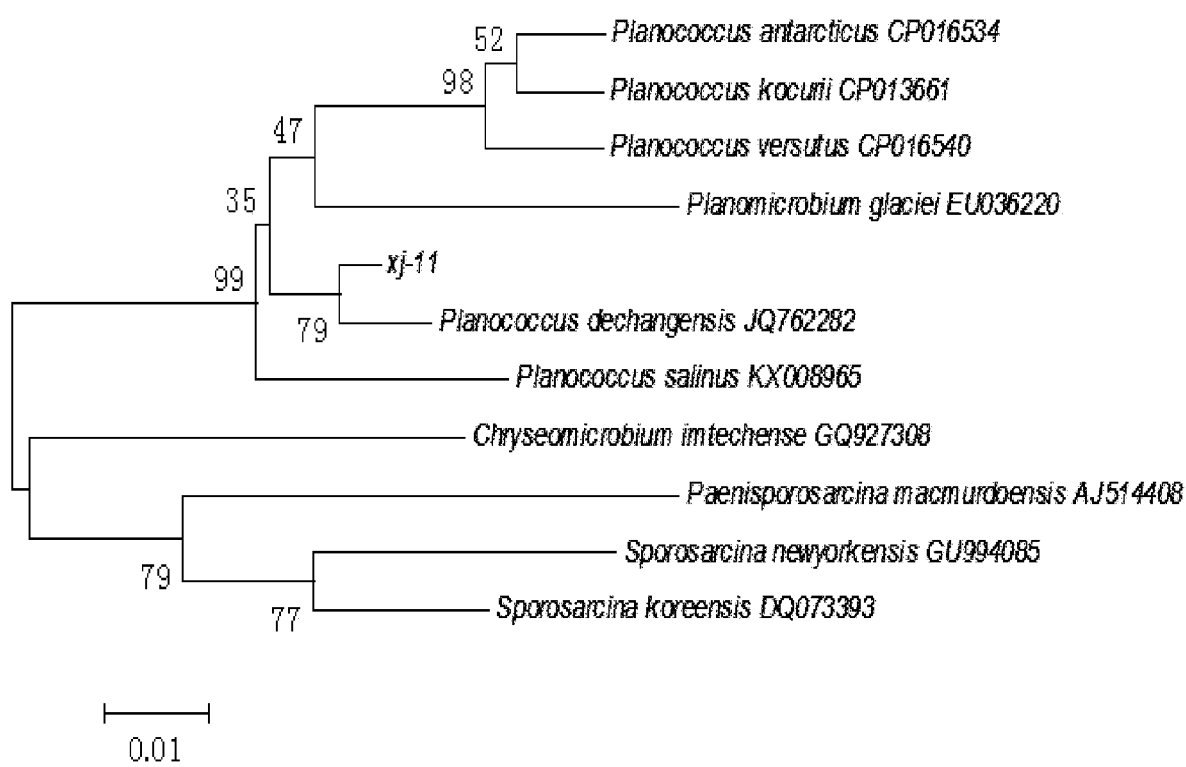
FIG. 6 shows the phylogenetic tree constructed by 16S rRNA sequence of the *Planococcus* strain *Planococcus* dechangensis XJ11.
Figure 7:
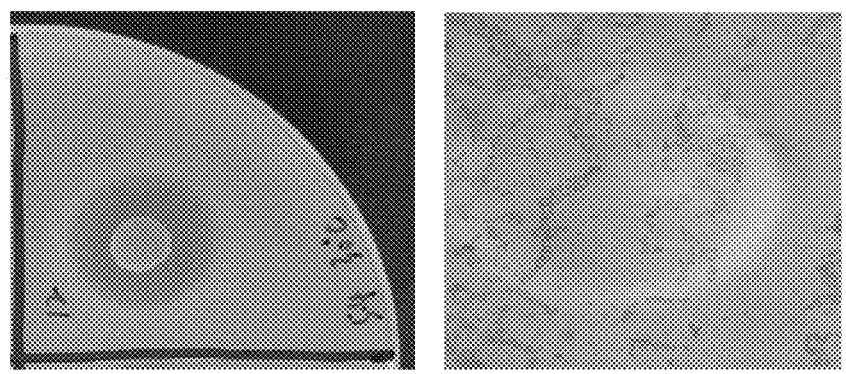
FIG. 7 shows the colony morphology and bacterial morphology of a *Planococcus* strain *Planococcus* rifietoensis XJ12.
Figure 8:
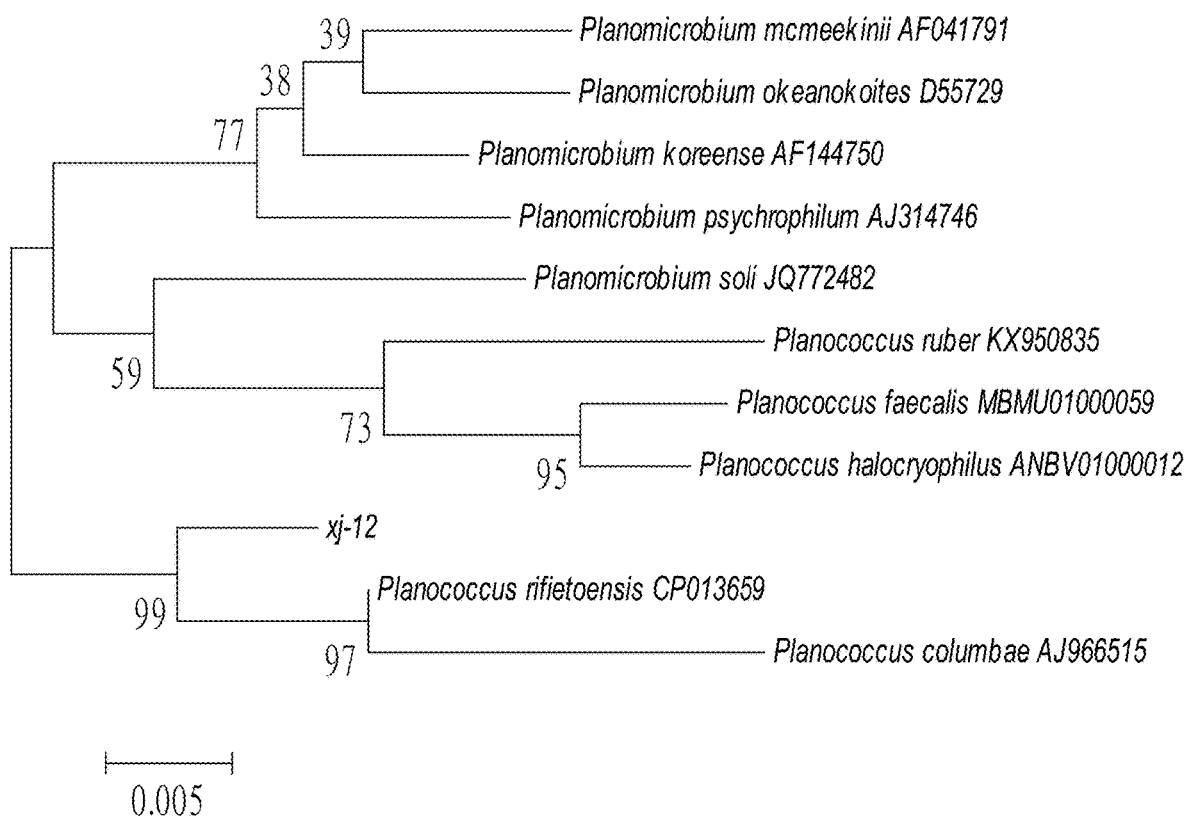
FIG. 8 shows the phylogenetic tree constructed by 16S rRNA sequence of the *Planococcus* strain *Planococcus* rifietoensis XJ12.

1. Screening and purification of strains:

Using traditional low-temperature fermented fresh shrimp paste (derived from a homemade shrimp paste in a farm restaurant in Weihai City, Shandong Province) as a raw material, the *Planococcus* producing low-temperature protease is separated and selected from the shrimp paste. The fresh shrimp paste is diluted and coated on a solid. Incubate the culture medium at 15° C. for 48 h, pick colonies with typical characteristics, carry out multiple streak separation and purification, and finally obtain a single colony of *Planococcus* that produce low-temperature protease. The isolated and purified single colony is inoculated on the inclined surface. Incubate at 25° C. for 24 h and store for future use.

2. Identification of Strains 2.1 Morphological Identification

The colonies are orange-yellow, with smooth surfaces, neat edges, opaqueness, and dense colonies; Gram staining is positive; the cells are spherical, arranged in a single or pile.

2.2 Physiological Characteristics

The 4 strains of *Planococcus* can grow when the NaCl concentration is 0-15%; when the pH is 7-9, they grow faster; they can grow well in the temperature range of 15° C.-35° C.;

2.3 Molecular Biology Identification

The 16S rRNA sequencing of the screened and purified *Planococcus* showed that the strains were *Planococcus maritimus, Planococcus plakortidis, Planococcus dechangensis*, and *Planococcus rifietoensis*, and the biological evolution relationship tree was constructed.

3. Deposit of Strains

*Planococcus maritimus* XJ2, this strain has been deposited on Jan. 2, 2019 in the China General Microbiological Culture Collection Center (CGMCC), numbered CGMCC NO. 17057, suggested classification name: *Planococcus maritimus*.

*Planococcus plakortidis* XJ10, this strain has been deposited on Jan. 2, 2019 in the China General Microbiological Culture Collection Center (CGMCC), numbered CGMCC NO. 17058, suggested classification name: *Planococcus plakortidis*.

*Planococcus dechangensis* XJ11, this strain has been deposited on Jan. 2, 2019 in the Chinese General Microbiological Culture Collection Center (CGMCC), numbered CGMCC NO. 17059, suggested classification name: *Planococcus dechangensis*.

*Planococcus rifietoensis* XJ12, which has been deposited on Jan. 2, 2019 in the Chinese General Microbiological Culture Collection Center (CGMCC), numbered CGMCC NO. 17060, suggested classification name: *Planococcus rifietoensis*.

Embodiment 1

A method for improving the fermentation quality of low-salt fish sauce by using strains of *Planococcus maritimus* XJ2, according to the following steps:

(1) Treatment of raw materials: The fish trimmings (wastes from fish flesh processing) were minced, and 5% (w/w) of a pickling sea salt was added, before mixing well for future use;

(2) Preparation of mixed starter: *Planococcus maritimus* XJ2 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus maritimus* XJ2 according to the final addition amount ($10^5$ CFU/mL) was mixed into the pretreated raw minced fish flesh, so that the final bacterial count can meet the addition requirements;

(4) Fermentation: The mixture obtained in step (3) is incubated and fermented at a temperature of 15° C. for 30 days;

(5) Filtration of fish sauce: The fish sauce sample obtained in step (4) was sterilized at 120° C. for 10 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 30 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with *Planococcus maritimus* XJ2 can reach 1.284 g/100 mL. According to the Chinese fish sauce industry standard, the fish sauce is classified as first-grade fish sauce; The volatile basic nitrogen content is 107 mg/100 mL; the histamine content is 19 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 2

A method for improving the fermentation quality of low-salt fish sauce by using strains of *Planococcus maritimus* XJ2, according to the following steps:

(1) Treatment of raw materials: The fish trimmings (wastes from fish flesh processing) were minced, and 10% (w/w) of a pickling sea salt was added, before mixing well for future use;

(2) Preparation of mixed starter: *Planococcus maritimus* XJ2 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus maritimus* XJ2 according to the final addition amount ($10^7$ CFU/mL) was mixed into the pretreated raw minced fish flesh, so that the final bacterial count can meet the addition requirements;

(4) Fermentation: The mixture obtained in step (3) is incubated and fermented at a temperature of 20° C. for 15 days;

(5) Filtration of fish sauce: The fish sauce sample obtained in step (4) was sterilized at 120° C. for 20 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 20 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with *Planococcus maritimus* XJ2 can reach 1.023 g/100 mL. According to the Chinese fish sauce industry standard, the fish sauce is classified as first-grade fish sauce; The volatile basic nitrogen content is 94 mg/100 mL; the histamine content is 17 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 3

A method for improving the fermentation quality of low-salt fish sauce by using strains of *Planococcus maritimus* XJ2, according to the following steps:

(1) Treatment of raw materials: The fish trimmings (wastes from fish flesh processing) were minced, and 15% (w/w) of a pickling sea salt was added, before mixing well for future use;

(2) Preparation of mixed starter: *Planococcus maritimus* XJ2 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus maritimus* XJ2 according to the final addition amount ($10^9$ CFU/mL) was mixed into the pretreated raw minced fish flesh, so that the final bacterial count can meet the addition requirements;

(4) Fermentation: The mixture obtained in step (3) is incubated and fermented at a temperature of 30° C. for 5 days;

(5) Filtration of fish sauce: The fish sauce sample obtained in step (4) was sterilized at 120° C. for 30 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 15 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus maritimus* XJ2 can reach 0.97 g/100 mL. According to the Chinese fish sauce industry standard, the fish sauce is classified as first-grade fish sauce; The volatile basic nitrogen content is 85 mg/100 mL; the histamine content is 11 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 4

A method for improving the fermentation quality of low-salt fish sauce by using strains of *Planococcus plakortidis* XJ10, according to the following steps:

(1) Treatment of raw materials: The fish trimmings (wastes from fish flesh processing) were minced, and 5% (w/w) of a pickling sea salt was added, before mixing well for future use;

(2) Preparation of mixed starter: *Planococcus plakortidis* XJ10 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus plakortidis* XJ10 according to the final addition amount ($10^5$ CFU/mL) was mixed into the pretreated raw minced fish flesh, so that the final bacterial count can meet the addition requirements;

(4) Fermentation: The mixture obtained in step (3) is incubated and fermented at a temperature of 15° C. for 30 days;

(5) Filtration of fish sauce: The fish sauce sample obtained in step (4) was sterilized at 120° C. for 10 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 30 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus plakortidis* XJ10 can reach 1.117 g/100 mL. According to the Chinese fish sauce industry standard, the fish sauce is classified as first-grade fish sauce; The volatile basic nitrogen content is 112 mg/100 mL; the histamine content is 20 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 5

A method for improving the fermentation quality of low-salt fish sauce by using strains of *Planococcus plakortidis* XJ10, according to the following steps:

(1) Treatment of raw materials: The fish trimmings (wastes from fish flesh processing) were minced, and 10% (w/w) of a pickling sea salt was added, before mixing well for future use;

(2) Preparation of mixed starter: *Planococcus plakortidis* XJ10 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus plakortidis* XJ10 according to the final addition amount ($10^7$ CFU/mL) was mixed into the pretreated raw minced fish flesh, so that the final bacterial count can meet the addition requirements;

(4) Fermentation: The mixture obtained in step (3) is incubated and fermented at a temperature of 20° C. for 15 days;

(5) Filtration of fish sauce: The fish sauce sample obtained in step (4) was sterilized at 120° C. for 20 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 20 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus plakortidis* XJ10 can reach 1.103 g/100 mL. According to the Chinese fish sauce industry standard, the fish sauce is classified as first-grade fish sauce; The volatile basic nitrogen content is 99 mg/100 mL; the histamine content is 18 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 6

A method for improving the fermentation quality of low-salt fish sauce by using strains of *Planococcus plakortidis* XJ10, according to the following steps:

(1) Treatment of raw materials: The fish trimmings (wastes from fish flesh processing) were minced, and 15% (w/w) of a pickling sea salt was added, before mixing well for future use;

(2) Preparation of mixed starter: *Planococcus plakortidis* XJ10 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus plakortidis* XJ10 according to the final addition amount ($10^9$ CFU/mL) was mixed into the pretreated raw minced fish flesh, so that the final bacterial count can meet the addition requirements;

(4) Fermentation: The mixture obtained in step (3) was incubated and fermented at a temperature of 30° C. for 5 days;

(5) Filtration of fish sauce: The fish sauce sample obtained in step (4) was sterilized at 120° C. for 30 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 15 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus plakortidis* XJ10 can reach 1.008 g/100 mL. According to the Chinese fish sauce industry standard, the fish sauce is classified as first-grade fish sauce; The volatile basic nitrogen content is 92 mg/100 mL; the histamine content is 17 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 7

A method for improving the fermentation quality of low-salt fish sauce by using strains of *Planococcus dechangensis* XJ11, according to the following steps:

(1) Treatment of raw materials: The fish trimmings (wastes from fish flesh processing) were minced, and 5% (w/w) of a pickling sea salt was added, before mixing well for future use;

(2) Preparation of mixed starter: *Planococcus dechangensis* XJ11 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus dechangensis* XJ11 according to the final addition amount ($10^5$ CFU/mL) was mixed into the pretreated raw minced fish flesh, so that the final bacterial count can meet the addition requirements;

(4) Fermentation: The mixture obtained in step (3) is incubated and fermented at a temperature of 15° C. for 30 days;

(5) Filtration of fish sauce: The fish sauce sample obtained in step (4) was sterilized at 120° C. for 10 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 30 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus dechangensis* XJ11 can reach 1.216 g/100 mL. According to the Chinese fish sauce industry standard, the fish sauce is classified as first-grade fish sauce; The volatile basic nitrogen content is 109 mg/100 mL; the histamine content is 19 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 8

A method for improving the fermentation quality of low-salt fish sauce by using strains of *Planococcus dechangensis* XJ11, according to the following steps:

(1) Treatment of raw materials: The fish trimmings (wastes from fish flesh processing) were minced, and 10% (w/w) of a pickling sea salt was added, before mixing well for future use;

(2) Preparation of mixed starter: *Planococcus dechangensis* XJ11 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus dechangensis* XJ11 according to the final addition amount ($10^7$ CFU/mL) was mixed into the pretreated raw minced fish flesh, so that the final bacterial count can meet the addition requirements;

(4) Fermentation: The mixture obtained in step (3) is incubated and fermented at a temperature of 20° C. for 15 days;

(5) Filtration of fish sauce: The fish sauce sample obtained in step (4) was sterilized at 120° C. for 20 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 20 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus dechangensis* XJ11 can reach 1.174 g/100 mL. According to the Chinese fish sauce industry standard, the fish sauce is classified as first-grade fish sauce; The volatile basic nitrogen content is 98 mg/100 mL; the histamine content is 20 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 9

A method for improving the fermentation quality of low-salt fish sauce by using strains of *Planococcus dechangensis* XJ11, according to the following steps:

(1) Treatment of raw materials: The fish trimmings (wastes from fish flesh processing) were minced, and 15% (w/w) of a pickling sea salt was added, before mixing well for future use;

(2) Preparation of mixed starter: *Planococcus dechangensis* XJ11 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus dechangensis* XJ11 according to the final addition amount ($10^9$ CFU/mL) was mixed into the pretreated raw minced fish flesh, so that the final bacterial count can meet the addition requirements;

(4) Fermentation: The mixture obtained in step (3) is incubated and fermented at a temperature of 30° C. for 5 days;

(5) Filtration of fish sauce: The fish sauce sample obtained in step (4) was sterilized at 120° C. for 30 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 15 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, the method refers to GB5009.208-2016 spectrophotometry.

(8) Physical and chemical index results of fish sauce: The amino acid content of the fish sauce fermented with this strain of *Planococcus dechangensis* XJ11 can reach 1.089 g/100 mL. According to the Chinese fish sauce industry standard, the fish sauce is classified as first-grade fish sauce; The volatile basic nitrogen content is 92 mg/100 mL; the histamine content is 14 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 10

A method for improving the fermentation quality of low-salt fish sauce by using strains of *Planococcus rifietoensis* XJ12, according to the following steps:

(1) Treatment of raw materials: The fish trimmings (wastes from fish flesh processing) were minced, and 5% (w/w) of a pickling sea salt was added, before mixing well for future use;

(2) Preparation of mixed starter: *Planococcus rifietoensis* XJ12 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus rifietoensis* XJ12 according to the final addition amount ($10^5$ CFU/mL) was mixed into the pretreated raw minced fish flesh, so that the final bacterial count can meet the addition requirements;

(4) Fermentation: The mixture obtained in step (3) is incubated and fermented at a temperature of 15° C. for 30 days;

(5) Filtration of fish sauce: The fish sauce sample obtained in step (4) was sterilized at 120° C. for 10 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 30 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus rifietoensis* XJ12 can reach 1.159 g/100 mL. According to the Chinese fish sauce industry standard, the fish sauce is classified as first-grade fish sauce; The volatile basic nitrogen content is 104 mg/100 mL; the histamine content is 16 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 11

A method for improving the fermentation quality of low-salt fish sauce by using strains of *Planococcus rifietoensis* XJ12, according to the following steps:

(1) Treatment of raw materials: The fish trimmings (wastes from fish flesh processing) were minced, and 10% (w/w) of a pickling sea salt was added, before mixing well for future use;

(2) Preparation of mixed starter: *Planococcus rifietoensis* XJ12 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus rifietoensis* XJ12 according to the final addition amount ($10^7$ CFU/mL) was mixed into the pretreated raw minced fish flesh, so that the final bacterial count can meet the addition requirements;

(4) Fermentation: The mixture obtained in step (3) is incubated and fermented at a temperature of 20° C. for 15 days;

(5) Filtration of fish sauce: The fish sauce sample obtained in step (4) was sterilized at 120° C. for 20 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 20 mins, and filled and sealed under aseptic conditions to obtain the finished fish sauce;

(7) Evaluation of product physical and chemical indicators: amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus rifietoensis* XJ12 can reach 1.207 g/100 mL. According to the Chinese fish sauce industry standard, the fish sauce is classified as first-grade fish sauce; The volatile basic nitrogen content is 109 mg/100 mL; the histamine content is 21 mg/100 mL, which is lower than the EU standard of 40 mg/100 mL. The earthy smell inherent in the raw material in this fish sauce is greatly reduced, and the umami taste is obvious. Compared with the fish sauce fermented by adding strains, the flavor has been significantly improved.

Embodiment 12

A method for improving the fermentation quality of low-salt fish sauce by using strains of *Planococcus rifietoensis* XJ12, according to the following steps:

(1) Treatment of raw materials: mince fish trimmings (wastes from fish flesh processing), add 15% (w/w) of a pickling sea salt, mix well for future use;

(2) Preparation of mixed starter: *Planococcus rifietoensis* XJ12 was activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of starter culture: *Planococcus rifietoensis* XJ12 according to the final addition amount ($10^9$ CFU/mL) was mixed into the pretreated raw minced fish flesh, so that the final bacterial count can meet the addition requirements;

(4) Fermentation: The mixture obtained in step (3) is incubated and fermented at a temperature of 30° C. for 5 days;

(5) Filtration of fish sauce: The fish sauce sample obtained in step (4) was sterilized at 120° C. for 30 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 15 mins, and filled and sealed under aseptic conditions to obtain the finished fish sauce;

(7) Evaluation of product physical and chemical indicators: amino acid nitrogen content evaluation, method refers to GB5009.235-2016 colorimetry; volatile basic nitrogen content evaluation, method refers to GB5009.228-2016 micro-diffusion method; determination of histamine content, the method refers to GB5009.208-2016 spectrophotometry.

(8) Physical and chemical index results of fish sauce: The amino acid content of the fish sauce fermented with this strain of *Planococcus rifietoensis* XJ12 can reach 1.012 g/100 mL. According to the Chinese fish sauce industry standard, the fish sauce is classified as first-grade fish sauce; The volatile basic nitrogen content is 98 mg/100 mL; the histamine content is 14 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 13

A method for improving the fermentation quality of low-salt fish sauce by using mixed *Planococcus* strains, according to the following steps:

(1) Treatment of raw materials: mince the fish trimmings (wastes from fish flesh processing), add 5% (w/w) of a pickling sea salt, mix well for future use;

(2) Preparation of mixed starter: *Planococcus maritimus* XJ2, *Planococcus plakortidis* XJ10, *Planococcus dechangensis* XJ11 and *Planococcus rifietoensis* XJ12 were separately activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of mixed starter: *Planococcus maritimus* XJ2, *Planococcus plakortidis* XJ10, *Planococcus dechangensis* XJ11 and *Planococcus rifietoensis* XJ12 were mixed according to the bacteria count ratio (1:1:1:1) to prepare the mixed starter, and according to the final addition amount ($10^5$ CFU/mL), the mixed starter was mixed into the pretreated raw minced fish flesh, so that the final bacterial count can meet the addition requirements;

(4) Fermentation: The mixture obtained in step (3) is incubated and fermented at a temperature of 15° C. for 5 days;

(5) Filtration of fish sauce: The fish sauce sample obtained in step (4) was sterilized at 120° C. for 10 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 30 mins, and filled and sealed under aseptic conditions to obtain the finished fish sauce;

(7) Evaluation of product physical and chemical indicators: amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus* can reach 0.974 g/100 mL. According to the Chinese fish sauce industry standard, the fish sauce is classified as first-grade fish sauce; The volatile basic nitrogen content is 113 mg/100 mL; the histamine content is 17 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 14

A method for improving the fermentation quality of low-salt fish sauce by using mixed *Planococcus* strains, according to the following steps:

(1) Treatment of raw materials: mince the fish trimmings (wastes from fish flesh processing), add 5% (w/w) of a pickling sea salt, mix well for future use;

(2) Preparation of mixed starter: *Planococcus maritimus* XJ2, *Planococcus plakortidis* XJ10, *Planococcus dechangensis* XJ11 and *Planococcus rifietoensis* XJ12 were separately activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of mixed starter: *Planococcus maritimus* XJ2, *Planococcus plakortidis* XJ10, *Planococcus dechangensis* XJ11 and *Planococcus rifietoensis* XJ12 were mixed according to the bacteria count ratio (1:2:2:1) to prepare the mixed starter, and according to the final addition amount ($10^5$ CFU/mL), the mixed starter was mixed into the pretreated raw minced fish flesh, so that the final bacterial count can meet the addition requirements;

(4) Fermentation: The mixture obtained in step (3) is incubated and fermented at a temperature of 15° C. for 30 days;

(5) Filtration of fish sauce: The fish sauce sample obtained in step (4) was sterilized at 120° C. for 10 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 30 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus* can reach 1.327 g/100 mL. According to the Chinese fish sauce industry standard, the fish sauce is classified as first-grade fish sauce; The volatile basic nitrogen content is 125 mg/100 mL; the histamine content is 23 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 15

A method for improving the fermentation quality of low-salt fish sauce by using mixed *Planococcus* strains, according to the following steps:

(1) Treatment of raw materials: mince the fish trimmings (wastes from fish flesh processing) with a meat mincer, add 8% (w/w) of a pickling sea salt, mix well for future use;

(2) Preparation of mixed starter: *Planococcus maritimus* XJ2, *Planococcus plakortidis* XJ10, *Planococcus dechangensis* XJ11 and *Planococcus rifietoensis* XJ12 were separately activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of mixed starter: *Planococcus maritimus* XJ2, *Planococcus plakortidis* XJ10, *Planococcus dechangensis* XJ11 and *Planococcus rifietoensis* XJ12 were mixed according to the bacteria count ratio (1:2:1:1) to prepare the mixed starter, and according to the final addition amount ($10^6$ CFU/mL), the mixed starter was mixed into the pretreated raw minced fish flesh, so that the final bacterial count can meet the addition requirements;

(4) Fermentation: The mixture obtained in step (3) is incubated and fermented at a temperature of 20° C. for 10 days;

(5) Filtration of fish sauce: The fish sauce sample obtained in step (4) was sterilized at 120° C. for 15 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 15 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus* can reach 1.034 g/100 mL. According to the Chinese fish sauce industry standard, the fish sauce is classified as first-grade fish sauce; The volatile basic nitrogen content is 119 mg/100 mL; the histamine content is 20 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 16

A method for improving the fermentation quality of low-salt fish sauce by using mixed *Planococcus* strains, according to the following steps:

(1) Treatment of raw materials: mince the fish trimmings (wastes from fish flesh processing), add 10% (w/w) of a pickling sea salt, mix well for future use;

(2) Preparation of mixed starter: *Planococcus maritimus* XJ2, *Planococcus plakortidis* XJ10, *Planococcus dechangensis* XJ11 and *Planococcus rifietoensis* XJ12 were separately activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of mixed starter: *Planococcus maritimus* XJ2, *Planococcus plakortidis* XJ10, *Planococcus dechangensis* XJ11 and *Planococcus rifietoensis* XJ12 were mixed according to the bacteria count ratio (1:2:1:2) to prepare the mixed starter, and according to the final addition amount ($10^6$ CFU/mL), the mixed starter was mixed into the pretreated raw minced fish flesh, so that the final bacterial count can meet the addition requirements;

(4) Fermentation: The mixture obtained in step (3) is incubated and fermented at a temperature of 20° C. for 15 days;

(5) Filtration of fish sauce: The fish sauce sample obtained in step (4) was sterilized at 120° C. for 15 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 15 mins, and filled and sealed under aseptic conditions to obtain the finished fish sauce;

(7) Evaluation of product physical and chemical indicators: amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus* can reach 1.116 g/100 mL. According to the Chinese fish sauce industry standard, the fish sauce is classified as first-grade fish sauce; The volatile basic nitrogen content is 108 mg/100 mL; the histamine content is 19 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 17

A method for improving the fermentation quality of low-salt fish sauce by using mixed *Planococcus* strains, according to the following steps:

(1) Treatment of raw materials: mince the fish trimmings (wastes from fish flesh processing), add 10% (w/w) of a pickling sea salt, mix well for future use;

(2) Preparation of mixed starter: *Planococcus maritimus* XJ2, *Planococcus plakortidis* XJ10, *Planococcus dechangensis* XJ11 and *Planococcus rifietoensis* XJ12 were separately activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of mixed starter: *Planococcus maritimus* XJ2, *Planococcus plakortidis* XJ10, *Planococcus dechangensis* XJ11 and *Planococcus rifietoensis* XJ12 were mixed according to the bacteria count ratio (3:1:1:2) to prepare the mixed starter, and according to the final addition amount ($10^7$ CFU/mL), the mixed starter was mixed into the pretreated raw minced fish flesh, so that the final bacterial count can meet the addition requirements;

(4) Fermentation: The mixture obtained in step (3) is incubated and fermented at a temperature of 25° C. for 20 days;

(5) Filtration of fish sauce: The fish sauce sample obtained in step (4) was sterilized at 120° C. for 30 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 15 mins, and filled and sealed under aseptic conditions to obtain the finished fish sauce;

(7) Evaluation of product physical and chemical indicators: amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus can reach* 1.124 g/100 mL. According to the Chinese fish sauce industry standard, the fish sauce is classified as first-grade fish sauce; The volatile basic nitrogen content is 110 mg/100 mL; the histamine content is 21 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 18

A method for improving the fermentation quality of low-salt fish sauce by using mixed *Planococcus* strains, according to the following steps:

(1) Treatment of raw materials: mince the fish trimmings (wastes from fish flesh processing), add 12% (w/w) of a pickling sea salt, mix well for future use;

(2) Preparation of mixed starter: *Planococcus maritimus* XJ2, *Planococcus plakortidis* XJ10, *Planococcus dechangensis* XJ11 and *Planococcus rifietoensis* XJ12 were separately activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of mixed starter: *Planococcus maritimus* XJ2, *Planococcus plakortidis* XJ10, *Planococcus dechangensis* XJ11 and *Planococcus rifietoensis* XJ12 were mixed according to the bacteria count ratio (1:1:2:1) to prepare the mixed starter, and according to the final addition amount ($10^8$ CFU/mL), the mixed starter was mixed into the pretreated raw minced fish flesh, so that the final bacterial count can meet the addition requirements;

(4) Fermentation: The mixture obtained in step (3) is incubated and fermented at a temperature of 25° C. for 25 days;

(5) Filtration of fish sauce: The fish sauce sample obtained in step (4) was sterilized at 120° C. for 30 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 15 mins, and filled and sealed under aseptic conditions to obtain the finished fish sauce;

(7) Evaluation of product physical and chemical indicators: amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus* can reach 1.009 g/100 mL. According to the Chinese fish sauce industry standard, the fish sauce is classified as first-grade fish sauce; The volatile basic nitrogen content is 112 mg/100 mL; the histamine content is 20 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 19

A method for improving the fermentation quality of low-salt fish sauce by using mixed *Planococcus* strains, according to the following steps:

(1) Treatment of raw materials: mince the fish trimmings (wastes from fish flesh processing), add 15% (w/w) of a pickling sea salt, mix well for future use;

(2) Preparation of mixed starter: *Planococcus maritimus* XJ2, *Planococcus plakortidis* XJ10, *Planococcus dechangensis* XJ11 and *Planococcus rifietoensis* XJ12 were separately activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of mixed starter: *Planococcus maritimus* XJ2, *Planococcus plakortidis* XJ10, *Planococcus dechangensis* XJ11 and *Planococcus rifietoensis* XJ12 were mixed according to the bacteria count ratio (1:1:3:1) to prepare the mixed starter, and according to the final addition amount ($10^9$ CFU/mL), the mixed starter was mixed into the pretreated raw minced fish flesh, so that the final bacterial count can meet the addition requirements;

(4) Fermentation: The mixture obtained in step (3) is incubated and fermented at a temperature of 30° C. for 5 days;

(5) Filtration of fish sauce: The fish sauce sample obtained in step (4) was sterilized at 120° C. for 20 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 25 mins, and filled and sealed under aseptic conditions to obtain the finished fish sauce;

(7) Evaluation of product physical and chemical indicators: amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus* can reach 0.873 g/100 mL. According to the Chinese fish sauce industry standard, the fish sauce is classified as first-grade fish sauce; The volatile basic nitrogen content is 97 mg/100 mL; the histamine content is 16 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

Embodiment 20

A method for improving the fermentation quality of low-salt fish sauce by using mixed *Planococcus* strains, according to the following steps:

(1) Treatment of raw materials: mince the fish trimmings (wastes from fish flesh processing), add 15% (w/w) of a pickling sea salt, mix well for future use;

(2) Preparation of mixed starter: *Planococcus maritimus* XJ2, *Planococcus plakortidis* XJ10, *Planococcus dechangensis* XJ11 and *Planococcus rifietoensis* XJ12 were separately activated and cultured three times; the activated bacterial suspension was centrifuged at 4° C. and 10000 r/min for 10 min, and then washed twice with sterile physiological saline, then resuspended in a small amount of sterile physiological saline, and finally adjust the bacterial suspension concentration to $10^5$-$10^7$ CFU/mL for future use;

(3) Addition of mixed starter: *Planococcus maritimus* XJ2, *Planococcus plakortidis* XJ10, *Planococcus dechangensis* XJ11 and *Planococcus rifietoensis* XJ12 were mixed according to the bacteria count ratio (3:3:3:3) to prepare the mixed starter, and according to the final addition amount ($10^9$ CFU/mL), the mixed starter was mixed into the pretreated raw minced fish flesh, so that the final bacterial count can meet the addition requirements;

(4) Fermentation: The mixture obtained in step (3) is incubated and fermented at a temperature of 30° C. for 30 days;

(5) Filtration of fish sauce: The fish sauce sample obtained in step (4) was sterilized at 120° C. for 20 mins, cooled to room temperature and centrifuged at 10000 r/min for 20 mins, and the supernatant was filtered with multiple layers of gauze to remove solids and impurities;

(6) Sterilization of fish sauce: The fish sauce obtained in step (5) is subjected to secondary sterilization at 100° C. for 25 mins, and filled and sealed under aseptic conditions to obtain the finished fish sauce;

(7) Evaluation of product physical and chemical indicators: Amino acid nitrogen content evaluation, method refers to GB5009.235-2016 colorimetry; volatile basic nitrogen content evaluation, method refers to GB5009.228-2016 micro-diffusion method; determination of histamine content, method refers to GB5009.208-2016 spectrophotometry.

(8) Physical and chemical index results of fish sauce: The amino acid content of the fish sauce fermented with this strain of *Planococcus* can reach 0.981 g/100 mL. According to the Chinese fish sauce industry standard, the fish sauce is classified as first-grade fish sauce; The volatile basic nitrogen content is 104 mg/100 mL; the histamine content is 18 mg/100 mL, which is lower than the EU standard of 40 mg/100 mL. The earthy smell inherent in the raw material in this fish sauce is greatly reduced, and the umami taste is obvious. Compared with the fish sauce produced by traditional fermentation, the flavor has been significantly improved.

What is claimed is:

1. A method for fermenting a fish sauce by using *Planococcus maritimus* XJ2, designated as CGMCC NO. 17057, the method comprises the following steps:
   (1) treatment of raw materials: mincing fish trimmings, which are wastes from fish flesh processing with a mincer, and adding 5 to 15% (w/w) of a pickling sea salt thereto, followed by mixing well;
   (2) preparation of starter cultures: activating and culturing *Planococcus maritimus* XJ2 three times to obtain an activated bacterial suspension; centrifuging the activated bacterial suspension at 4° C. and 10000 r/min for 10 min to obtain cell pellets, and washing the cell pellets twice with sterile physiological saline, resuspending the cell pellets in a small amount of the sterile physiological saline to obtain a bacterial suspension, and finally adjusting a concentration of the bacterial suspension to $10^5$-$10^7$ CFU/mL;
   (3) addition of the starter cultures: mixing the strain into the pretreated raw minced fish flesh to obtain a mixture, so that the final bacterial count meets a final addition amount of $10^5$-$10^9$ CFU/g;
   (4) fermentation of fish sauce: incubating and fermenting the mixture obtained in step (3) at a temperature of 15-30° C. for 5-30 days;
   (5) filtration of the fish sauce: sterilizing the fish sauce sample obtained in step (4) at 120° C. for 10 to 30 mins, cooling the sterilized fish sauce sample to room temperature and centrifuging it at 10000 r/min for 20 mins to obtain a supernatant, and filtering the supernatant with multiple layers of gauze to remove solids and impurities; and
   (6) sterilization of the fish sauce: performing secondary sterilization on the fish sauce obtained in step (5) at 100° C. for 15 to 30 mins, followed by filling and sealing it under aseptic conditions to obtain a finished fish sauce.

2. A method for shortening a fermentation cycle of a low-salt fish sauce by using mixed *Planococcus* strains, comprising the following steps:
   (1) treatment of raw materials: mincing fish trimmings, which are wastes from fish flesh processing with a mincer, and adding 5 to 15% (w/w) of a pickling sea salt thereto, followed by mixing well;
   (2) preparation of mixed starter: activating and culturing each of *Planococcus maritimus* XJ2, *Planococcus plakortidis* XJ10, *Planococcus dechangensis* XJ11 and *Planococcus rifietoensis* XJ12 three times to obtain an activated bacterial suspension; centrifuging the activated bacterial suspension at 4° C. and 10000 r/min for 10 min to obtain cell pellets, and washing the cell pellets twice with sterile physiological saline, resuspending the cell pellets in a small amount of the sterile physiological saline to obtain a bacterial suspension, and finally adjusting a concentration of the bacterial suspension to $10^5$-$10^7$ CFU/mL;
   (3) addition of the mixed starter: mixing *Planococcus maritimus* XJ2, *Planococcus plakortidis* XJ10, *Planococcus dechangensis* XJ11 and *Planococcus rifietoensis* XJ12 according to a bacteria count ratio of (1-3):(1-3):(1-3):(1-3) to prepare the mixed starter, and mixing the mixed starter into the pretreated raw minced fish flesh to obtain a mixture, so that the final bacterial count meets a final addition amount of $10^5$-$10^9$ CFU/g;
   (4) fermentation of fish sauce: incubating and fermenting the mixture obtained in step (3) at a temperature of 15-30° C. for 5-30 days;
   (5) filtration of the fish sauce: sterilizing the fish sauce sample obtained in step (4) at 120° C. for 10 to 30 mins, cooling the sterilized fish sauce sample to room temperature and centrifuging it at 10000 r/min for 20 mins to obtain a supernatant, and filtering the supernatant with multiple layers of gauze to remove solids and impurities; and
   (6) sterilization of the fish sauce: performing secondary sterilization on the fish sauce obtained in step (5) at 100° C. for 15 to 30 mins, followed by filling and sealing it under aseptic conditions to obtain a finished fish sauce.

3. A method for fermenting a fish sauce by using *Planococcus plakortidis* XJ10, designated as CGMCC NO. 17058, the method comprises the following steps:
   (1) treatment of raw materials: mincing fish trimmings, which are wastes from fish flesh processing with a mincer, and adding 5 to 15% (w/w) of a pickling sea salt thereto, followed by mixing well;
   (2) preparation of starter cultures: activating and culturing *Planococcus plakortidis* XJ10 three times to obtain an activated bacterial suspension; centrifuging the activated bacterial suspension at 4° C. and 10000 r/min for 10 min to obtain cell pellets, and washing the cell pellets twice with sterile physiological saline, resuspending the cell pellets in a small amount of the sterile physiological saline to obtain a bacterial suspension, and finally adjusting a concentration of the bacterial suspension to $10^5$-$10^7$ CFU/mL;
   (3) addition of the starter cultures: mixing the strain into the pretreated raw minced fish flesh to obtain a mixture, so that the final bacterial count meets a final addition amount of $10^5$-$10^9$ CFU/g;
   (4) fermentation of fish sauce: incubating and fermenting the mixture obtained in step (3) at a temperature of 15-30° C. for 5-30 days;

(5) filtration of the fish sauce: sterilizing the fish sauce sample obtained in step (4) at 120° C. for 10 to 30 mins, cooling the sterilized fish sauce sample to room temperature and centrifuging it at 10000 r/min for 20 mins to obtain a supernatant, and filtering the supernatant with multiple layers of gauze to remove solids and impurities; and (6) sterilization of the fish sauce: performing secondary sterilization on the fish sauce obtained in step (5) at 100° C. for 15 to 30 mins, followed by filling and sealing it under aseptic conditions to obtain a finished fish sauce.

4. A method for fermenting a fish sauce by using *Planococcus dechangensis* XJ11, designated as CGMCC NO. 17059, the method comprises the following steps:

(1) treatment of raw materials: mincing fish trimmings, which are wastes from fish flesh processing with a mincer, and adding 5 to 15% (w/w) of a pickling sea salt thereto, followed by mixing well;

(2) preparation of starter cultures: activating and culturing *Planococcus dechangensis* XJ11 three times to obtain an activated bacterial suspension; centrifuging the activated bacterial suspension at 4° C. and 10000 r/min for 10 min to obtain cell pellets, and washing the cell pellets twice with sterile physiological saline, resuspending the cell pellets in a small amount of the sterile physiological saline to obtain a bacterial suspension, and finally adjusting a concentration of the bacterial suspension to $10^5$-$10^7$ CFU/mL;

(3) addition of the starter cultures: mixing the strain into the pretreated raw minced fish flesh to obtain a mixture, so that the final bacterial count meets a final addition amount of $10^5$-$10^9$ CFU/g;

(4) fermentation of fish sauce: incubating and fermenting the mixture obtained in step (3) at a temperature of 15-30° C. for 5-30 days;

(5) filtration of the fish sauce: sterilizing the fish sauce sample obtained in step (4) at 120° C. for 10 to 30 mins, cooling the sterilized fish sauce sample to room temperature and centrifuging it at 10000 r/min for 20 mins to obtain a supernatant, and filtering the supernatant with multiple layers of gauze to remove solids and impurities; and (6) sterilization of the fish sauce: performing secondary sterilization on the fish sauce obtained in step (5) at 100° C. for 15 to 30 mins, followed by filling and sealing it under aseptic conditions to obtain a finished fish sauce.

5. A method for fermenting a fish sauce by using the *Planococcus rifietoensis* XJ12, designated as CGMCC NO. 17060, the method comprises the following steps:

(1) treatment of raw materials: mincing fish trimmings, which are wastes from fish flesh processing with a mincer, and adding 5 to 15% (w/w) of a pickling sea salt thereto, followed by mixing well;

(2) preparation of starter cultures: activating and culturing *Planococcus rifietoensis* XJ12 three times to obtain an activated bacterial suspension; centrifuging the activated bacterial suspension at 4° C. and 10000 r/min for 10 min to obtain cell pellets, and washing the cell pellets twice with sterile physiological saline, resuspending the cell pellets in a small amount of the sterile physiological saline to obtain a bacterial suspension, and finally adjusting a concentration of the bacterial suspension to $10^5$-$10^7$ CFU/mL;

(3) addition of the starter cultures: mixing the strain into the pretreated raw minced fish flesh to obtain a mixture, so that the final bacterial count meets a final addition amount of $10^5$-$10^9$ CFU/g;

(4) fermentation of fish sauce: incubating and fermenting the mixture obtained in step (3) at a temperature of 15-30° C. for 5-30 days;

(5) filtration of the fish sauce: sterilizing the fish sauce sample obtained in step (4) at 120° C. for 10 to 30 mins, cooling the sterilized fish sauce sample to room temperature and centrifuging it at 10000 r/min for 20 mins to obtain a supernatant, and filtering the supernatant with multiple layers of gauze to remove solids and impurities; and (6) sterilization of the fish sauce: performing secondary sterilization on the fish sauce obtained in step (5) at 100° C. for 15 to 30 mins, followed by filling and sealing it under aseptic conditions to obtain a finished fish sauce.

\* \* \* \* \*